United States Patent
Christensen

(10) Patent No.: US 6,471,954 B2
(45) Date of Patent: Oct. 29, 2002

(54) METHOD FOR THE PRODUCTION AND USE OF A CREAM CONTAINING VITAMIN-A

(75) Inventor: Flemming Kjærgaard Christensen, Hadsund (DK)

(73) Assignee: Cortex Technology ApS, Hadsund (DK)

( * ) Notice: Subject to any disclaimer, the term of this patent is extended or adjusted under 35 U.S.C. 154(b) by 0 days.

(21) Appl. No.: 09/767,836

(22) Filed: Jan. 24, 2001

(65) Prior Publication Data

US 2002/0137790 A1 Sep. 26, 2002

(51) Int. Cl.[7] ............... A61K 31/74; A61K 7/42; C07D 311/76
(52) U.S. Cl. ............ 424/78.06; 424/59; 549/408; 568/671; 514/458; 514/725
(58) Field of Search ............... 549/401, 408; 568/671; 424/401, 400, 489, 59, 78.06; 514/458, 904, 969, 725

(56) References Cited

U.S. PATENT DOCUMENTS 4,224,319 A * 9/1980 Marcadet ............ 424/238
4,457,918 A * 7/1984 Holick et al. ......... 424/180

* cited by examiner

Primary Examiner—Alan L. Rotman
Assistant Examiner—Rita Desai

(74) Attorney, Agent, or Firm—Antonelli, Terry, Stout & Kraus, LLP

(57) ABSTRACT

A method for the production of a vitamin-A containing cream comprising the following steps:

a) a first mixture—consisting of a number of water-soluble substances such as glycerine and extracts of plants—is mixed together during heating and comminution until the mixture has a temperature of about some 80° C., preferably 83° C., b) a second mixture consisting of a number of oil-soluble substances, including emulsifiers, and squalane and vegetable oils such as avocado oil are mixed together during heating until the mixture has a temperature of about some 80° C., preferably 83° C., c) said first mixture is then gradually added to said second mixture during high-shear-mixing with decreasing number of revolutions—from about 5000 rpm to about 3300 rpm—until the temperature of the mixture slowly has decreased to about some 50° C., preferably 51° C., d) said last mixture is then added to a third mixture containing of alpha-tocopherol, tocopherol acetate, retinyl palmitate and retinyl acetate preferably in the following mutual relation 10:50:61:58—determined in accordance with the used mixture of vitamines, e) the final mixture is then successively homogenized at a pressure of about 1000 bar and then kept at constants temperature of some 50° C., until the whole mixture is homogenized, whereafter the mixture is high-shear-mixed with decreasing number of revolution until the temperature is about some 40° C., preferable 45° C., f) finally, the viscosity of the cream is adjusted by stirring.

16 Claims, No Drawings

METHOD FOR THE PRODUCTION AND USE OF A CREAM CONTAINING VITAMIN-A

FIELD OF THE INVENTION

The present invention relates to a method for the production of a vitamin-A containing cream primary for skin care.

BACKGROUND OF THE INVENTION

Vitamin-A is an endogenous compound which occurs naturally in the human body and is essential for normal epithelial cell differentiation. Natural and synthetic vitamin-A derivatives have been used extensively in the treatment of a variety of skin disorders and have been used as skin repair and renewal agents.

The purpose of the invention is to provide a new and improved method for the production of a vitamin-A containing cream which may be used for general skin care and furthermore may be used for preparation of the skin prior to treatment by plastic or cosmetic surgery.

SUMMARY OF THE INVENTION

According to the present invention there is provided a method for the production of a vitamin-A containing cream comprising the following steps:

a) a first mixture—consisting of a number of water-soluble substances such as glycerine and extracts of plants—is mixed together during heating and comminution until the mixture has a temperature of about some 80° C., preferably 83° C., b) a second mixture consisting of a number of oil-soluble substances, including emulsifiers, and squalane and vegetable oils such as avocado oil are mixed together during heating until the mixture has a temperature of about some 80° C., preferably 83° C., c) said first mixture is then gradually added to said second mixture during high-shear-mixing with decreasing number of revolutions—from about 5000 rpm to about 3300 rpm—until the temperature of the mixture slowly has decreased to about some 50° C., preferably 51° C., d) said last mixture is then added to a third mixture containing of alpha-tocopherol, tocopherol acetate, retinyl palmitate and retinyl acetate preferably in the following mutual relation 10:50:61:58—determined in accordance with the used mixture of vitamines, e) the final mixture is then successively homogenized at a pressure of about 1000 bar and then kept at constants temperature of some 50° C., until the whole mixture is homogenized, whereafter the mixture is high-shear-mixed with decreasing number of revolutions until the temperature is about some 40° C., preferable 45° C., f) finally, the viscosity of the cream is adjusted by stirring.

Tests of the vitamin-A cream produced by the method stated have shown that the very small vitamine-A preparations presumeable due to the high pressure homogenization in combination with the effective shear treatment of the final mixture and due to the presence of the squalane—which itself is an oleaginous substance—are able to penetrate direct into the very small (nmeter sized) oil drops of the oil in water emulsion state of the cream production.

As a consequence this means that the vitamin-A preparations contained in the oil drops of the cream by applying this to the skin in a similar manner due to the presence of the squalane are able to penetrate deeper than the basal cells of the epidermal tissue and act as skin repair and renewal agents.

Preferably by the method according to the invention the content relation between avocado oil and squalene of said second mixture is about 400:500, preferable 425:490.

By the method according to the invention the final mixture after high-pressure-homogenization is high-shear-mixed at a rate of revolution decreasing from about 400–3000 rpm, preferable 3500 rpm, to about 2000–2600 rpm, preferable 2300 rpm.

According to the invention the final adjustment of viscosity of the cream is carried out after some time period of at least about 12 hours—allowing proper emulsification of the cream—and at room temperature i.e. at a temperature about 20°–30° C.

The present invention furthermore relates to a method of using the vitamin-A containing cream produced by the method according to the invention for the preparation of the skin prior to plastic or cosmetic surgery executed by laser technology and similar surgical treatments, e.g. dermabrasion, by which the outmost possibly wrinkled layers of the epidermal tissue are removed in order to recover a smooth and healthy epidermis wherein the skin area to be treated prior to the surgical treatment is extensively preparated by applying the cream to the skin during a period of time of at least 7–21 days, preferable 14 days, prior to the surgical treatment.

Preferably by the method of use according to the invention the preparation of the skin area to be treated is carried out more times during the day and used also as a night time cream.

In the following the invention is explained in more details by means of a number of examples:

EXAMPLE 1

| | |
|---|---|
| Water | 67,31% |
| Phenova | 0,70% |
| Na-Lactate | 1,00% |
| EDTA | 0,10% |
| Glycerine | 6,00% |
| Cetyl-alcohol | 1,52% |
| Glyceryl Stearate PEG 100 | 4.75% |
| Stearic Acid | 0,80% |
| Behenyl-alcohol | 1,00% |
| Lanolin | 1,50% |
| Cetearyl-alcohol and PEG 20 Stearate | 1,00% |
| Dioctylsuccinate | 2,00% |
| Avocado Oil | 3,19% |
| Octylmethoxycinnemate | 4,00% |
| Squalane | 3,67% |
| Alpha-tocopherol | 0,08% |
| Tocopherol acetate | 0,38% |
| Retinyl palmitate | 0,46% |
| Retinyl acetate | 0,42% |
| Perfume | 0,12% |

EXAMPLE 2

| | |
|---|---|
| Water | 63,51% |
| Phenova | 0,70% |
| Na-Lactate | 1,00% |
| EDTA | 0,10% |
| Glycerine | 6,00% |
| Cetyl-alcohol | 1,52% |
| Glyceryl Stearate PEG 100 | 5,25% |
| Stearic Acid | 1,00% |
| Behenyl-alcohol | 1,00% |

-continued

| | |
|---|---|
| Lanolin | 1,50% |
| Cetearyl-alcohol and PEG 20 Stearate | 1,50% |
| Dioctylsuccinate | 2,00% |
| Avocado Oil | 4,56% |
| Octylmethoxycinnemate | 4,00% |
| Squalane | 5,27% |
| Alpha-tocopherol | 0,11% |
| Tocopherol acetate | 0,54% |
| Retinyl palmitate | 0,66% |
| Retinyl acetate | 0,60% |
| Perfume | 0,12% |

What is claimed is:

1. A method for producing a vitamin A-containing cream, the method comprising the steps of
   (a) preparing a first mixture by combining at least one water soluble substance selected from glycerine, EDTA and sodium lactate, and extracts of plants during heating and comminuting until the mixture has a temperature of about 80–83° C.;
   (b) preparing a second mixture by mixing emulsifiers, squalane, and at least one vegetable oil during heating until the mixture has a temperature of about 80–83° C.;
   (c) preparing a third mixture by gradually adding the first mixture of step (a) to the second mixture of step (b) during high-shear mixing with a decreasing number of revolutions from about 5000 rpm to about 3000 rpm and while allowing the mixture to cool to a temperature of about 50–51° C.;
   (d) preparing a fourth mixture by combining alpha-tocopherol, tocopherol acetate, retinyl palmitate and retinyl acetate;
   (e) adding the fourth mixture of step (d) to the third mixture of step (c) to create a fifth mixture;
   (f) homogenizing the fifth mixture of step (e) at a pressure of about 1000 bar and at a temperature of about 50° C.;
   (g) subjecting the homogenized mixture of step (f) to high-shear-mixing with a decreasing number of revolutions while allowing the homogenized mixture to cool to a temperature of about 40–45° C. to create a cream; and
   (h) adjusting the viscosity of the cream by stirring.

2. The method of claim 1 wherein the water soluble substance of the first mixture of step (a) is glycerine.

3. The method of claim 1 wherein the heating of step (a) is to a temperature of 83° C.

4. The method of claim 1 wherein the vegetable oil in the second mixture of step (b) is avocado oil and wherein the ratio of avocado oil and squalane is about 400:500.

5. The method of claim 1 wherein the vegetable oil in the second mixture of step (b) is avocado oil and wherein the ratio of avocado oil and squalene is about 425:490.

6. The method of claim 1 wherein the heating of step (b) is to a temperature of 83° C.

7. The method of claim 1 wherein in step (c), the third mixture is cooled to a temperature of 51° C.

8. The method of claim 1 wherein the ratio of alpha-tocopherol, tocopherol acetate, retinyl palmitate and retinyl acetate in the fourth mixture is 10:50:61:58.

9. The method of claim 1 wherein the high-shear-mixing with a decreasing number of revolutions in step (g) is carried out from a starting rate of about 4000–3000 rpm to a decreased rate of about 2600–2000 rpm.

10. The method of claim 1 wherein the high-shear-mixing with a decreasing number of revolutions in step (g) is carried out from a starting rate of 3500 rpm to a decreased rate of 2300 rpm.

11. The method of claim 1 wherein in step (g), the homogenized mixture is cooled to a temperature of 45° C.

12. The method of claim 1 wherein step (h) of adjusting the viscosity of the cream by stirring is carried out at least 12 hours after step (g) and wherein between step (g) and step (h), the cream is allowed to cool to a temperature of about 20 to 30° C.

13. The method of preparing skin for plastic or cosmetic surgical treatment, the method comprising the step of applying a vitamin A-containing cream prepared by the method of claim 1 to the skin for a period of about 7 to 21 days prior to the plastic or cosmetic surgical treatment.

14. The method of claim 13 wherein the cream is applied to the skin for a period of 14 days prior to the plastic or cosmetic surgical treatment.

15. The method of claim 13 wherein the cream is applied to the skin both during the day and during the night in the period prior to the plastic or cosmetic surgical treatment and wherein the cream is applied more times during the day than during the night.

16. The method of claim 10 wherein the plastic or cosmetic surgical treatment is dermabrasion.

* * * * *